(12) United States Patent
Bullard et al.

(10) Patent No.: US 9,888,897 B2
(45) Date of Patent: Feb. 13, 2018

(54) HIGH DYNAMIC RANGE MAMMOGRAPHY USING A RESTRICTED DYNAMIC RANGE FFDM

(71) Applicant: Dexela Limited, London (GB)

(72) Inventors: Edward Bullard, London (GB); Spencer Gunn, London (GB); James Brodrick, Slinfold (GB); Hamdan Amin, Stanmore (GB)

(73) Assignee: Dexela Limited, London (GB)

( * ) Notice: Subject to any disclaimer, the term of this patent is extended or adjusted under 35 U.S.C. 154(b) by 0 days.

(21) Appl. No.: 14/956,087

(22) Filed: Dec. 1, 2015

(65) Prior Publication Data

US 2016/0081647 A1    Mar. 24, 2016

Related U.S. Application Data

(63) Continuation of application No. 13/977,970, filed as application No. PCT/EP2012/051650 on Feb. 1, 2012, now Pat. No. 9,230,311.

(Continued)

(51) Int. Cl.
| | |
|---|---|
| *A61B 6/00* | (2006.01) |
| *G06T 5/00* | (2006.01) |
| *G06T 5/50* | (2006.01) |

(52) U.S. Cl.
CPC .......... *A61B 6/5229* (2013.01); *A61B 6/4233* (2013.01); *A61B 6/482* (2013.01);
(Continued)

(58) Field of Classification Search
CPC ...................................... A61B 6/502
See application file for complete search history.

(56) References Cited

U.S. PATENT DOCUMENTS

| | | | |
|---|---|---|---|
| 2002/0154802 A1 | 10/2002 | Goldkuhl | |
| 2006/0050843 A1* | 3/2006 | Strommer | .............. A61B 6/502 |
| | | | 378/37 |

(Continued)

FOREIGN PATENT DOCUMENTS

| | | |
|---|---|---|
| DE | 10 2005 026940 | 12/2006 |
| WO | WO 03/075764 | 9/2003 |

OTHER PUBLICATIONS

International Report on Patentability for PCT/EP2012/051650, dated Aug. 15, 2013, 8 pages.

(Continued)

*Primary Examiner* — Dani Fox
(74) *Attorney, Agent, or Firm* — Laurence & Phillips IP Law (57) ABSTRACT

Methods of imaging a breast comprising acquiring a sequence of image data sets having differing exposure parameters; and combining the image data sets into a mammography image having greater dynamic range than the dynamic range of any single component image data set. Disclosed methods may further comprise determining an exposure parameter of one or more component image data sets prior to acquiring the sequence of image data sets. The step of determining an exposure parameter of one or more component image data sets may comprise determining exposure duration or an exposure irradiation level. Also disclosed are mammography apparatus and systems to obtain images according to the disclosed methods.

28 Claims, 10 Drawing Sheets

Related U.S. Application Data (60) Provisional application No. 61/438,544, filed on Feb. 1, 2011.

(52) U.S. Cl.
CPC .............. *A61B 6/502* (2013.01); *A61B 6/542* (2013.01); *G06T 5/009* (2013.01); *G06T 5/50* (2013.01); *G06T 2207/10116* (2013.01); *G06T 2207/20208* (2013.01); *G06T 2207/20221* (2013.01); *G06T 2207/30068* (2013.01)

(56) References Cited

U.S. PATENT DOCUMENTS

| | | | |
|---|---|---|---|
| 2007/0025514 A1 | 2/2007 | Lawaczeck | |
| 2008/0037703 A1* | 2/2008 | Ting | A61B 6/466 378/37 |
| 2009/0213987 A1 | 8/2009 | Stein | |
| 2010/0034450 A1* | 2/2010 | Mertelmeier | A61B 6/032 382/131 |
| 2011/0157154 A1* | 6/2011 | Bernard | G06T 11/60 345/419 |

OTHER PUBLICATIONS

Wu et al. (2003) Medical Physics 30(3):365-380 "Tomographic mammography using a limited number of low-dose cone-beam projection images".

* cited by examiner

Fig. 16

HIGH DYNAMIC RANGE MAMMOGRAPHY USING A RESTRICTED DYNAMIC RANGE FFDM

RELATED APPLICATIONS

This application is a continuation of U.S. patent application Ser. No. 13/977,970 filed Jul. 2, 2013, entitled "High Dynamic Range Mammography Using a Restricted Dynamic Range FFDM," which claims priority to 35 USC § 371 of PCT Application Serial No. PCT/EP2012/051650, filed Feb. 1, 2012, entitled "High Dynamic Range Mammography Using a Restricted Dynamic Range FFDM," which claims priority to U.S. Provisional Application No. 61/438,544, filed Feb. 1, 2011, entitled "High Dynamic Range Mammography Using a Restricted Dynamic Range FFDM," which are each incorporated herein in their entirety by reference.

TECHNICAL FIELD

The embodiments disclosed herein relate to apparatus and methods of exposing and processing high dynamic range images from digital flat-panel x-ray detectors.

BACKGROUND

Flat panel detectors are used in mammography for screening and diagnostic imaging. In both cases it is desirable to see features over the full extent of the breast, from the thickest and most dense tissue near the chest wall and in the centre of the breast, such as fibroglandular breast tissue, to the thinnest and least dense tissue near the skin boundary, such as fat and skin. A full-breast mammography image is thus obtained from x-ray signals of wide dynamic range, ranging from the maximum intensity of a nearly unobstructed x-ray beam transmitted through the skin boundary, to the substantially weakened signal transmitted through dense tissue. The presentation of a useable wide dynamic range image is achieved in film-based methods by the use of high-latitude film, which has a non-linear response and can tolerate overexposure.

Digital mammography however, typically uses flat panel detectors that behave differently than film when exposed to varying intensities of exposure. One type of flat panel detector employs CMOS image sensors, which have an inherently linear response with poor latitude. In particular, sensors with small well size respond to overexposure by saturating. Saturation occurs when the sensor pixel values reach a constant maximum as a certain signal level is exceeded, and all data above this level is lost. CMOS image sensors however, are advantageous for mammography in that a well designed sensor will generate a low level of electronic noise, which provides enhanced contrast in dense breast tissue when compared to other types of flat panel detector.

The visibility of structures within the breast tissue is limited by the contrast-to-noise ratio (CNR) of the imaging system. The contrast of an object in a mammography image depends on the density of the object, the total x-ray attenuation provided by the object and the soft tissue in the breast, the x-ray spectrum used (photon energy and tube voltage kVp), scattered radiation and the display conditions. In addition, a non-saturating mammography exposure must be scaled to the unobstructed (air) transmission value. This can leave clinically significant areas of interest (denser tissue) underexposed, with consequently poor CNR.

The embodiments disclosed herein are directed toward overcoming one or more of the problems discussed above.

SUMMARY OF THE EMBODIMENTS

The disclosed embodiments include a method and associated apparatus which combines separate images of the breast into a single Full Field Digital Mammogram (FFDM), where the FFDM is composed of pixels of limited electron-well size that do not innately provide sufficient dynamic range to acquire a single-exposure mammogram showing detail in all relevant portions of a breast.

The described images are taken as a set of predetermined exposures and do not use image data recursively. The component images are then combined into a single presentation image using selected image recombination techniques. The disclosed methods differ from other previously taught methods in several aspects. For example, the disclosed methods apply to the field of mammography where every part of the breast, from dense tissue to near-transparent skin edges, must be imaged with a high level of image quality. In addition, the disclosed methods apply specifically to digital flat panel detectors where the electron well depth is designed to be below around 500 electrons per square micron, for minimisation of readout noise, which increases as a function of full well capacity.

Embodiments include a method of imaging a breast comprising acquiring a sequence of image data sets having differing exposure parameters; and combining the image data sets into a mammography image having greater dynamic range than the dynamic range of any single component image data set. Disclosed methods may further comprise determining an exposure parameter of one or more component image data sets prior to acquiring the sequence of image data sets. The step of determining an exposure parameter of one or more component image data sets may comprise determining exposure duration or an exposure irradiation level. The determination of an exposure parameter may be based upon one or more of; x-ray beam quality, x-ray beam intensity, information about the imaged object, breast thickness, patient age and the response of the detector.

The disclosed methods of imaging a breast of may be implemented using a digital flat panel detector designed for the minimisation of readout noise. For example, the digital flat panel detector electron well density can be designed to be below around 500 electrons per square micron.

An alternative embodiment is an apparatus for imaging a breast comprising: an x-ray source; an x-ray detector; and image processing apparatus configured to acquiring a sequence of image data sets having differing exposure parameters and combine the image data sets into a mammography image having greater dynamic range than the dynamic range of any single component image data set. The apparatus may comprise a digital flat panel detector designed for the minimisation of readout noise. for example, the digital flat panel detector electron well density can be designed to be below around 500 electrons per square micron.

An alternative embodiment is a system for obtaining a high dynamic range image of a breast, the system comprising: a mammography imaging device; and a data processing device providing for the combination of image data having lesser dynamic range obtained with the mammography imaging device into a mammography image having greater dynamic range.

An alternative embodiment is a computer readable storage medium having instructions stored thereon, wherein the instructions are implemented to provide a method of imaging a breast comprising: acquiring a sequence of image data sets having differing exposure parameters; and combining the image data sets into a mammography image having greater dynamic range than the dynamic range of any single component image data set.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The contrast of a region in an object in a mammography image depends on the density of the region, the x-ray attenuation of the region in the breast, the x-ray spectrum (photon energy, filtration, tube current, exposure length and tube voltage kVp), scattered radiation and the display conditions. The noise present in the image is the vector total of all noise processes contributing in the image chain. These noise contributors include:

i. Statistical variation (shot noise) of incident transmitted x-ray photons
ii. fixed pattern noise due to pixel offset variations,
iii. fixed pattern noise due to pixel gain variations,
iv. fixed pattern noise due to x-ray conversion and attenuation variations across the image applied by the scintillator and the covering materials,
v. temporal noise generated in the pixel during readout,
vi. temporal noise generated in amplifier stages prior to analogue-to-digital conversion,
vii. quantization noise introduced by the analogue-to-digital conversion,
viii. temporal noise introduced by rounding in subsequent data processing, and
ix. structural and temporal noise introduced by the display medium.

Noise sources ii, iii, iv, vi, vii, viii and ix can be addressed using known image acquisition, image processing or data manipulation techniques.

Noise source i; shot noise, is a function of the dose delivered to the breast, and the efficiency of the x-ray to photoelectron conversion. The delivered dose per image is limited by clinical restrictions relating to patient safety.

Noise source v; readout noise, is significant where a pixel's electrical output is low relative to its maximum value. Readout noise is limited by the design of the sensor and its physical limits. Readout noise is additive noise arising from the noise characteristics of semiconductor devices, which has the following general form:

$$S(\omega) \propto \begin{cases} \omega^{-b} & \omega < \omega_{min} \quad \beta > 0 \\ A & \omega_{min} < \omega < \omega_{max} \\ \omega^{\alpha} & \omega > \omega_{max} \quad \alpha > 0 \end{cases}$$

where A, $\alpha$ and $\beta$ are constants, and $\omega$ is the readout frequency. $\omega_{min}$ is the 1/f noise 'knee' below which the noise has a mainly 1/f characteristic.

In addition, there is a thermal noise contribution with theoretical lower limit $$\sigma_{KTC} = \sqrt{(kT/C)}$$

where k is the Boltzmann constant, T is the absolute temperature and C is the capacitance of the pixel.

It can be seen from the above that thermal noise increases with capacitance. Therefore, in general, the pixel capacitance or 'well size' should be minimised to reduce total readout noise. However, well size minimization also reduces the number of photoelectrons that can be recorded by a single pixel readout, since the voltage across the capacitor is limited to an upper value determined by the sensor design, and the voltage is proportional to the number of photoelectrons:

$$V_{MAX} = Ne^-/C$$

where N is the number of photoelectrons, and C is the capacitance. The practical effect of a small well size is that the sensor saturates ($V=V_{MAX}$) at a lower x-ray exposure.

Mammography, unlike most other types of radiography, must present clinically significant detail over the entire target including skin boundary. Mammography requires a high dynamic range from the imaging device in order to produce acceptable image quality contrast to noise ratio (CNR) from all parts of the breast within an exposure. However, high X-ray dynamic range requires a large well size, while the low readout noise that provides good contract in dense breast tissue requires a low well size. There is therefore a compromise required: a low noise detector does not provide a wide x-ray dynamic range, and a high dynamic range detector presents greater noise issues.

In particular, the read-out noise per pixel of a CMOS detector increases with the well capacity of the pixel. The maximum signal obtainable before saturation increases linearly with the well capacity. In order to maximize the signal-to-noise ratio for a given exposure dose, it can be shown that it is better to acquire multiple frames using a low-well-capacity pixel design, rather than a single frame using a high-well-capacity design, since the increase in total readout noise which results from multiple frame reads is more than offset by the reduction in readout noise due to the smaller well capacity. Therefore it is beneficial to use multiple-frame image acquisition in mammography as disclosed herein. In summary, multiple frame acquisition can be exploited to solve a problem which is particular to mammography, which is the problem of acquiring and presenting a clinically useful image from a subject which has a very wide x-ray transmission contrast ratio.

Figure 1:
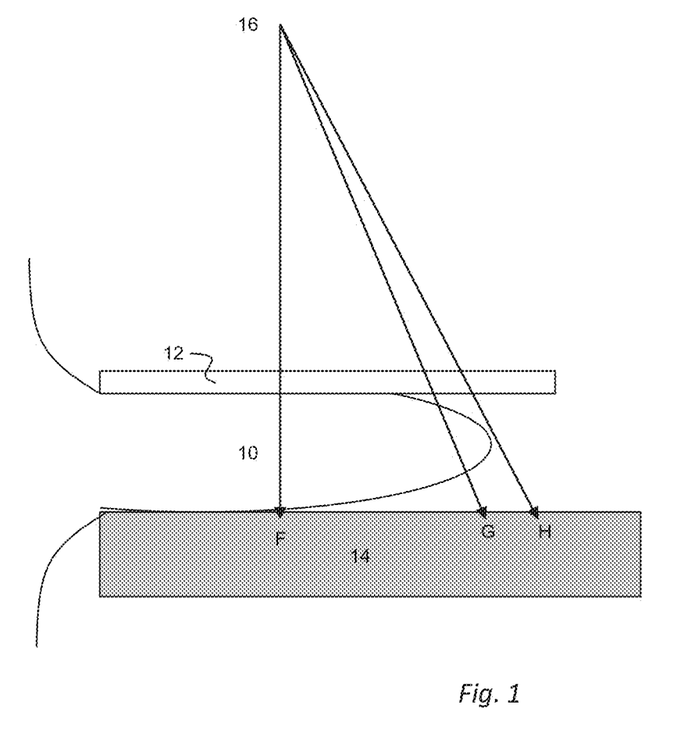
FIG. 1 is a schematic cross-section of a breast B positioned for a mammogram.

The problems unique to high dynamic range mammography using digital sensors may be more fully appreciated with respect to FIGS. 1-4. FIG. 1 shows a cross-section of a breast 10 positioned for a mammogram. An x-ray transparent compression plate 12 and a detector assembly 14 hold the breast immobile during x-ray exposure from a source 16. The resulting projection onto the detector 14 has a wide range of image intensities, as the x-rays are attenuated by different amounts ranging from no tissue attenuation (H), through partial attenuation (G), to maximum attenuation (F) where the rays pass through the thickest, densest tissue.

Figure 2:
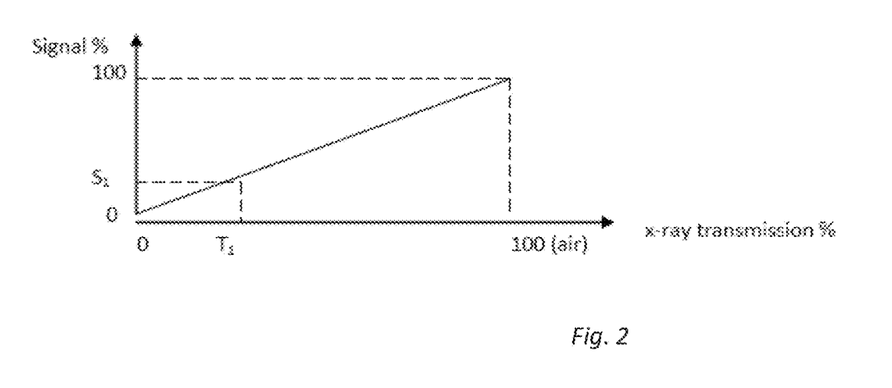
FIG. 2 is a graphic representation of a linear, low-gain response from a digital detector, where 100% of the digital pixel value corresponds to nominal zero x-ray attenuation.

FIG. 2 shows a linear, low-gain response from a digital detector, where 100% of the digital pixel value corresponds to nominal zero x-ray attenuation (air only). At an x-ray transmission $T_1$, the signal $S_1$ is large enough to represent usable clinical data. This is the linear response of a typically implemented Full Field Digital Mammography (FFDM) detector idealised for mammography where the maximum transmission (air with no tissue) generates the maximum response. Below transmission level $T_1$, in even denser regions of the breast for example, the CNR is unacceptable due to insufficient signal relative to readout noise.

Figure 3:
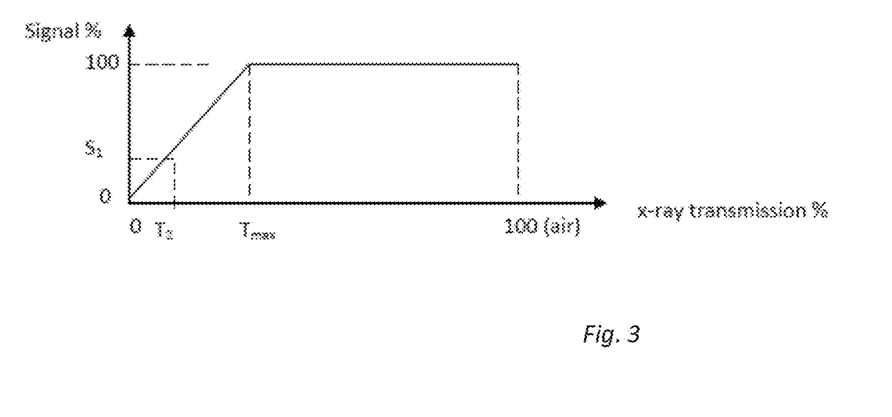
FIG. 3 is a graphic representation of a linear, high-gain response from a digital detector, where 100% of the digital pixel value corresponds to a transmission TMAX which is within the transmission range of the breast.

FIG. 3 shows a linear, high-gain response from a digital detector, where 100% of the digital pixel value corresponds to a transmission $T_{MAX}$ which is within the transmission range of the breast. The same effect would occur if the exposure dose, the x-ray beam energy, the x-ray tube current, or a combination of one or more of these parameters were increased. Any transmission higher than $T_{MAX}$ is represented by a uniform, saturated pixel output at 100%. The usable signal level $S_1$ now corresponds to a lower transmission level, $T_2$. An exposure such as is represented in FIG. 3 can be taken to acquire data which is missing from the exposure represented in FIG. 2 where the transmission level is less than $T_1$ and was too low to produce useable data. Such a mammogram would show image detail in denser regions but would show a monochrome grey value in less dense regions.

Figure 4:
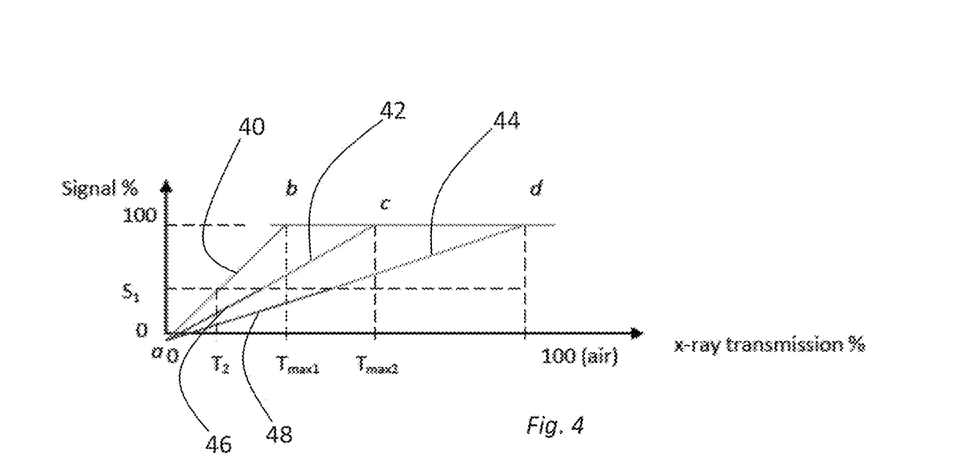
FIG. 4 is a graphic representation of a combination of three exposures of varying gain.

FIG. 4 shows a combination of three exposures of varying gain; exposures (ad) and (ab) are the exposures from FIG. 2 and FIG. 3 respectively. Above the transmission level $T_1$, the usable response is indicated by grey sections of each response curve. A third exposure (ac) is added, to fill in the midrange response between ad and ab. A third or successive intermediate exposure is not essential to the disclosed embodiments but may be used where there is a wide gain difference between the low and high-gain exposures.

As noted above, a set of two or more exposures with different exposure doses may be taken to extend the dynamic range of a selected sensor. At least one of the exposures should be capable of registering the air value (100% transmission) before saturation, as illustrated in FIG. 2. As described in detail below, the set of exposures may be prescribed according to a priori knowledge of the detector noise characteristics and the transmission of the densest region of interest in the breast.

In FIG. 4, the grey portion of each response curve (curve segments 40, 42 and 44 respectively) represent usable data. The portions of each response curve at 100% signal have no data because of sensor saturation. Finally, the portions of the response curves 46 and 48 have no useful data because the SNR due to readout noise is lower than 1, meaning that the data would contribute more noise than signal if it were used to compute a final result.

Figure 5:
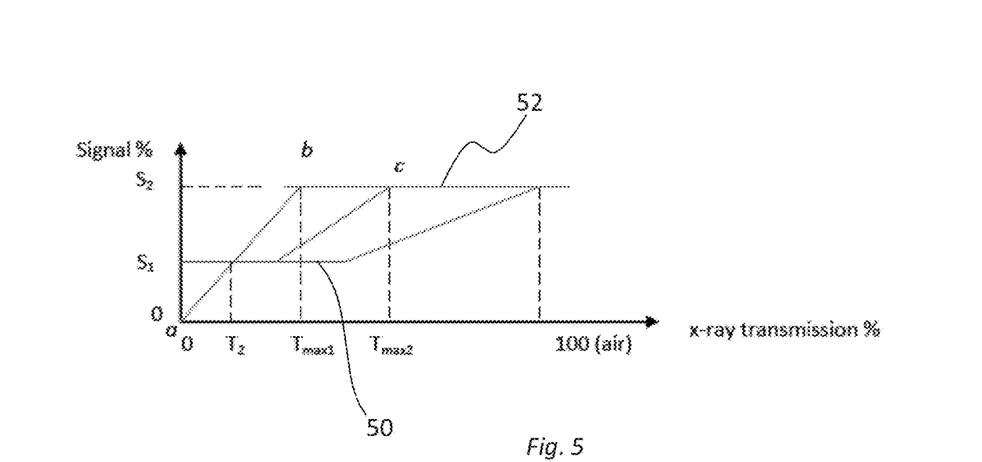
FIG. 5 is a graphic representation of thresholded image data from FIG. 4.

The usable data, for example data represented by response curves 40, 42 and 44 on FIG. 4, can be combined or fused into a high quality image using various techniques. The techniques include methods such as tone mapping and cross correlation. An example of a simple method of fusing is thresholding and addition. FIG. 5 graphically illustrates such a method using the data of FIG. 4. In the FIG. 5 representation, there is a lower noise thresholding process. In particular, the noisiest portions of data as illustrated on FIG. 4 (represented by response curve portions 46 and 48) are replaced by constants, shown as line 50 of FIG. 5. Therefore:

$$S' = \begin{cases} S_1 & S < S_1 \\ S & S > S_1 \end{cases}$$

The FIG. 5 representation also illustrates a numerical upper saturation thresholding process, represented by the upper line 52, since the actual saturation limits on the sensor may be subject to noise. Accordingly:

$$S' = \begin{cases} S & S < S_1 \\ S_2 & S > S_2 \end{cases}$$

Figure 6:
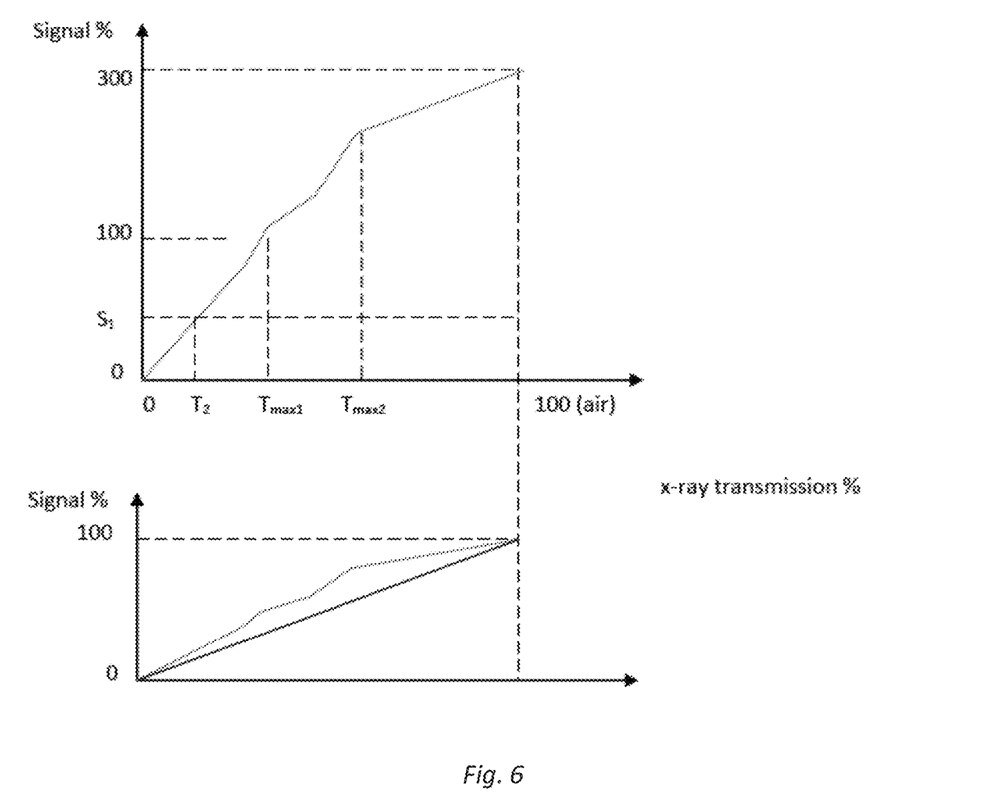
FIG. 6 is a graphic representation of combined image data from FIG. 4 and FIG. 5.

As shown in FIG. 6, adding the useful signals 40, 42 and 44 from all three images represented in FIGS. 4 and 5 yields a nonlinear but monotonic response to density, which demonstrates latitude, i.e. a reduction in sensitivity as the signal increases. X-ray film demonstrates a similar property of latitude.

Further refinements to this method can provide for different nonlinear responses. One side-effect of combining images in this way is the discontinuity in SNR, and therefore image quality, near the thresholds $T_{MAX1}$ and $T_{MAX2}$. This may be presented as contouring artifacts or bands visible as the density changes smoothly over the image. Known methods of image processing may be used to even out this discontinuity.

According to one embodiment, multiple exposures may be acquired within the duration of a single x-ray exposure. An FFDM device maybe programmed to acquire a sequence $$\frac{\delta S}{\delta T}$$

of images, the only difference between images being the frame integration time, which corresponds to the gain of the imager, or a sequence of exposures may be determined such that the maximum image information is acquired using the minimum duration of x-ray exposure. This can be achieved by definition of a threshold where image information contributes more noise than signal. Alternatively, a sequence of images may be obtained by varying the exposure level is between images, by varying the x-ray beam energy, the x-ray tube current or a combination of one or more of these parameters. To allow a sequence of images to be acquired without extending the duration of the imaging, the detector used must have a high read-out speed, for example 5 or more frames per second. Lengthening the imaging time would increase the risk of patient motion.

Figure 7:
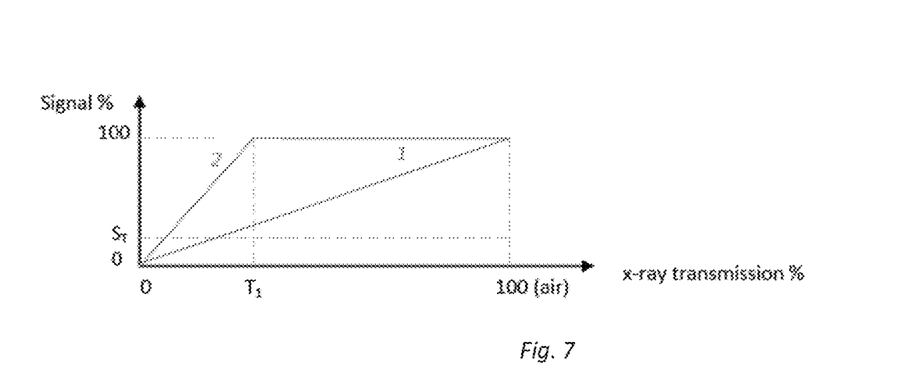
FIG. 7 is a graphic representation of two component exposure that may be combined to form a single HDR mammogram.

As noted above, two essential image features or regions in a FFDM are dense tissue information and substantially less dense skin edge information. As illustrated in FIG. 7, skin edge information may be acquired from a first exposure [1] which is short enough so that the unobstructed (air) values do not cause sensor saturation. The exposure time for exposure [1] can be determined from given data about the x-ray beam quality and intensity, and is not dependent on the image object.

Dense tissue information can be acquired through a second, longer or more intense exposure [2]. The exposure time for exposure [2] can be determined from given data about the x-ray beam quality and intensity, information about the imaged object (for example breast thickness, patient age, etc), and the response of the detector. Alternatively the exposure time for exposure [2] can be determined from analysis of exposure [1], where the correct exposure time is extrapolated from analysis of the trial exposure as follows:

$$t_2 = \begin{cases} t_1 \times S_{DT}/S_{DI} & t < t_{MAX} \\ t_{MAX} & t > t_{MAX} \end{cases}$$

where $t_1$ is the first exposure time [1], $S_{ST}$ is the required signal level in the densest part of the image, $S_{D1}$ is the signal level in the densest part of the image from the first exposure [1], and $t_{MAX}$ is an upper limit on exposure time imposed by restrictions on radiation dose.

Figure 8:
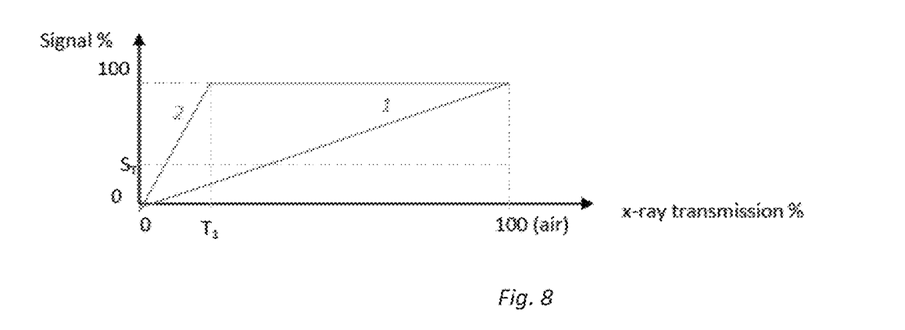
FIG. 8 is a graphic representation of two component exposure that are not suitable for combination to form a single HDR mammogram since the SNR of one sub-image is too low.
Figure 9:
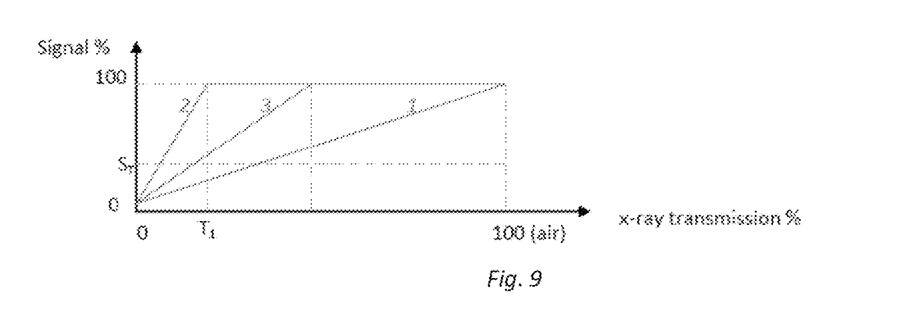
FIG. 9 is a graphic representation of three component exposure that may be combined to form a single HDR mammogram.

In some cases, two exposures will be sufficient if, in regions where the transmission is high enough to saturate the second exposure ($T>T_1$), the first exposure has enough signal to yield sufficient SNR (signal>$S_T$, where $S_T$ is the minimum signal to yield acceptable SNR). This is the case illustrated in FIG. 7. In other cases, one or more additional images [3] may be needed if, as shown in FIG. 8, the SNR from image [1] at transmission=$T_1$ is too low. This case is illustrated in FIG. 9. The set of images and exposure times can be thus be determined according to a logical process.

The input parameter $T_1$ can be determined by a priori knowledge of data concerning the imaged breast, using clinical data and look-up tables based upon the patients' age, breast thickness, the x-ray beam quality, etc.

Figure 10:
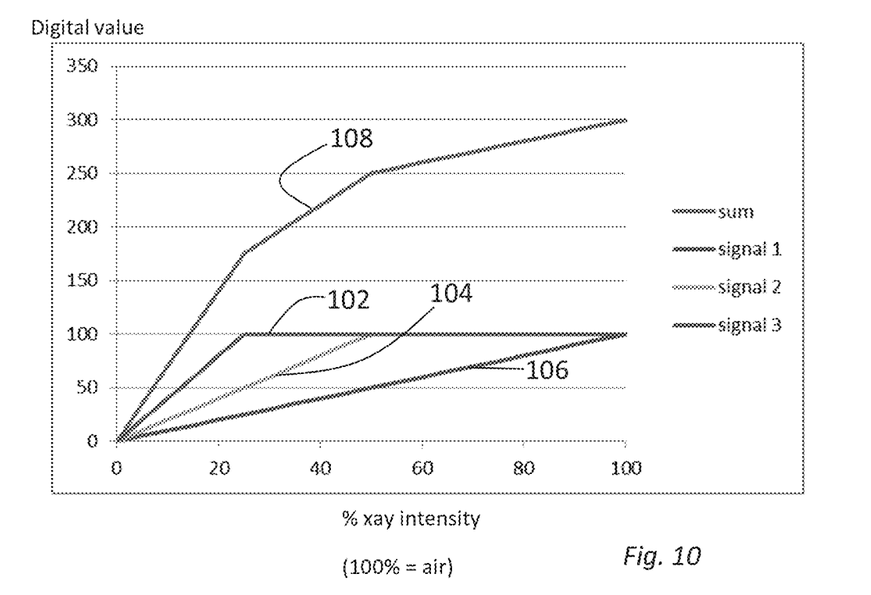
FIG. 10 is a graphic representation of a summation of a set of three images with different exposure levels performed where the images have equal weights.

The methods generally described above are more specifically described with respect to FIG. 10. Two or more sub-images, at different levels, are acquired in rapid succession on a single X-ray exposure at each selected view angle. These sub-images are then combined into a final image where both dense-tissue information and skin-edge information are presented. The exposure level is varied between images by varying the exposure duration, the x-ray beam energy, the x-ray tube current or a combination of one or more of these parameters.

Within the imager device, the pixel data from each image is bounded to a constant value $N_{SAT}$ which is lower than the saturation value of the image. A lower value is used because each pixel has a slightly different saturation level, and a global value ensures consistency across all pixels. Pixels with values above $N_{SAT}$ will therefore not contribute data to the composite image. The bounded image data is then combined. This can be done in a number of ways, for example:

(a) As shown in FIG. 10, a summation of a set of images with different exposure levels may be performed where the images have equal weights; this avoids contouring effects in the combined image as noted above. For sub-images 102, 104 and 106 (FIG. 10) the combined image $I_c$ is a summation:

$$I_C = \Sigma_{n=1}^M I_{(n)}$$

(b) Alternatively, summation of each image may be performed according to a weighting map, where the contribution from each image is varied over X and Y, according to some means of a priori image content analysis.

Example

A practical implementation of an image fusion process, which applies to mammography, is as described below with respect to FIGS. 11-15. The disclosed method identifies the best quality of each image, before combining the set using a scalar weighting values.

Appropriate scalar weight values are obtained from the relative exposure and contrast information which are taken directly from each image. Once the weight values are determined, the set of 'N' images is combined using weight blending:

$$B_{ij} = \Sigma_{k=1}^N W_{ij,k} J_{ij,k} \tag{1}$$

where J and W are pre-processed image and weight respectively. The pre-processed image 'J' is obtained by:

$$J = (L - L_{min})/(L_{max} - L_{min}) \tag{2}$$

where:

$$L = \left(\frac{I}{I_{max}}\right)^{1/2}$$

with 'I' being the input image.

The weight in equation (1) is normalized so that the sum of all weights of each pixel across the 'N' number of images is one:

$$\hat{W}_{ij,k} = \frac{W_{ij,k}}{\sum_{n=1}^{N} W_{ij,n}} \quad (3)$$

Here, the weight 'W' is determined by the exposure level and contrast measurement of each pixel.

$$W_{ij,k} = (E_{ij,k})^{we}(C_{ij,k})^{wc} \quad (4)$$

For the contrast 'C', absolute value of Laplacian filtering is used to highlight the edges. For the exposure level measurement 'E', the pixels with values closer to the central region of 0.5 is given more weight. This is done through a Gaussian curve. In this case, the effect of the pixels with intensities near the 0 (under-exposed) and 1 (over-exposed) are reduced. The weights therefore are obtained using:

$$W_{i,j} = \exp\left(-\frac{(J_{ij} - 0.5)^2}{2\sigma^2}\right) \quad (5)$$

Figure 11:
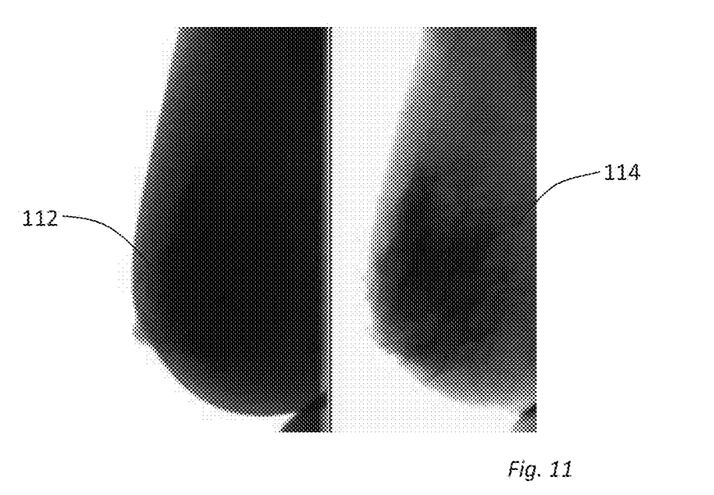
FIG. 11 is two x-ray images of a breast taken at lower and higher exposures.
Figure 12:
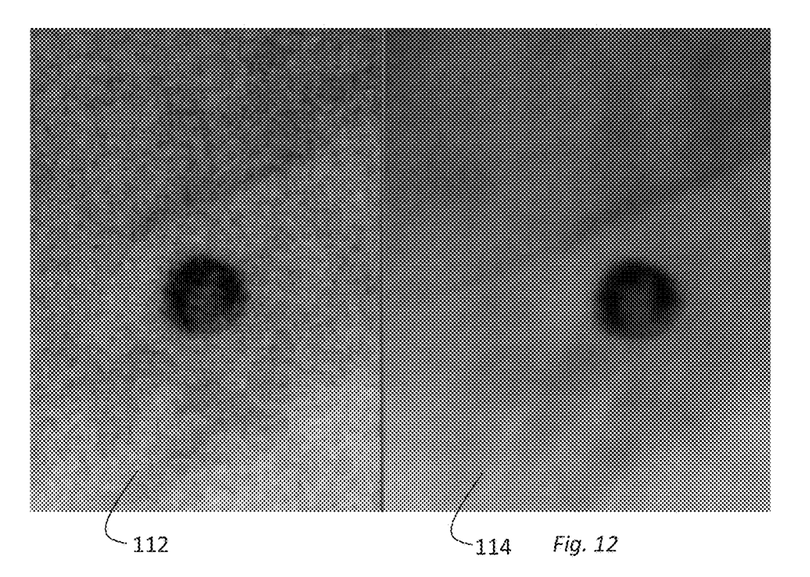
FIG. 12 is a magnified view of the two x-ray images of FIG. 11.
Figure 13:
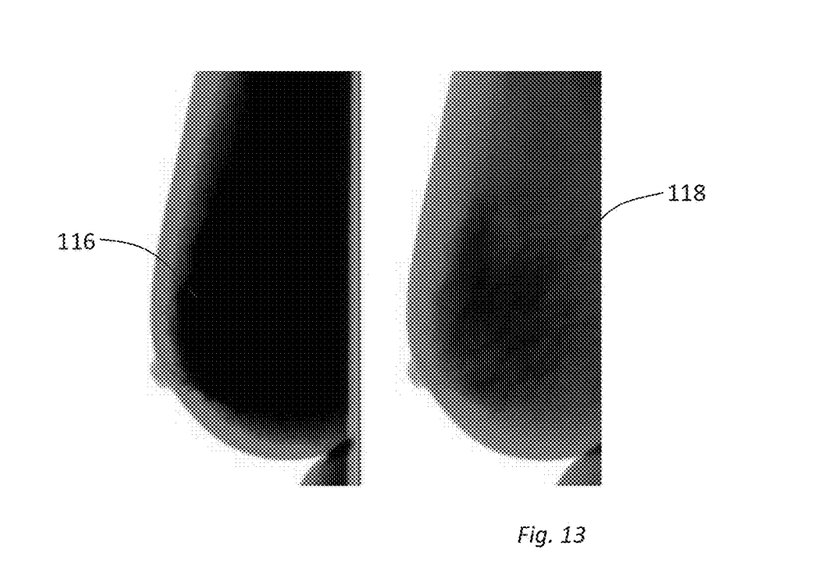
FIG. 13 is two x-ray images showing an average of the lower exposure and higher exposure of FIG. 11 and a weight blending of the lower exposure and higher exposure of FIG. 11.
Figure 14:
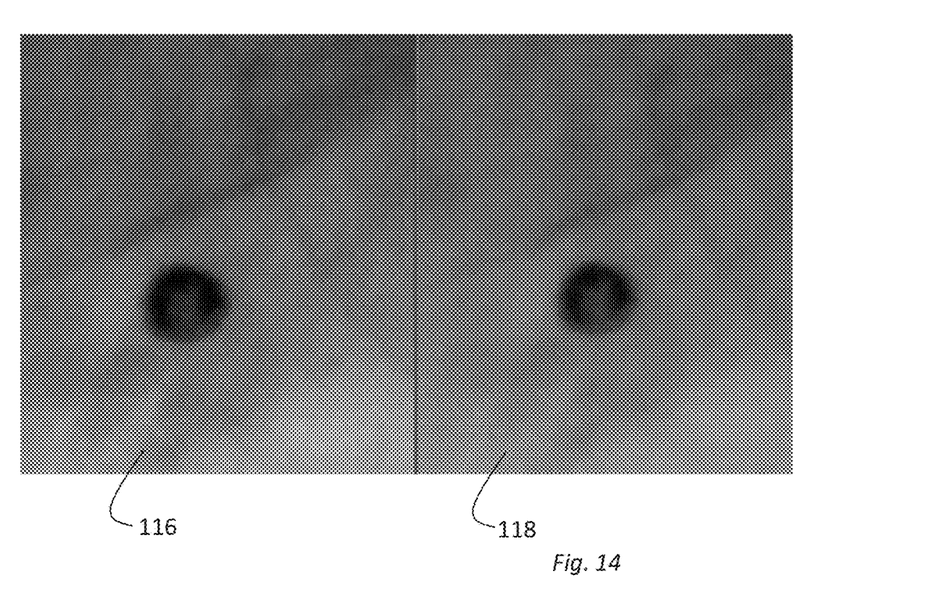
FIG. 14 is a magnified view of the two x-ray images of FIG. 13.
Figure 15:
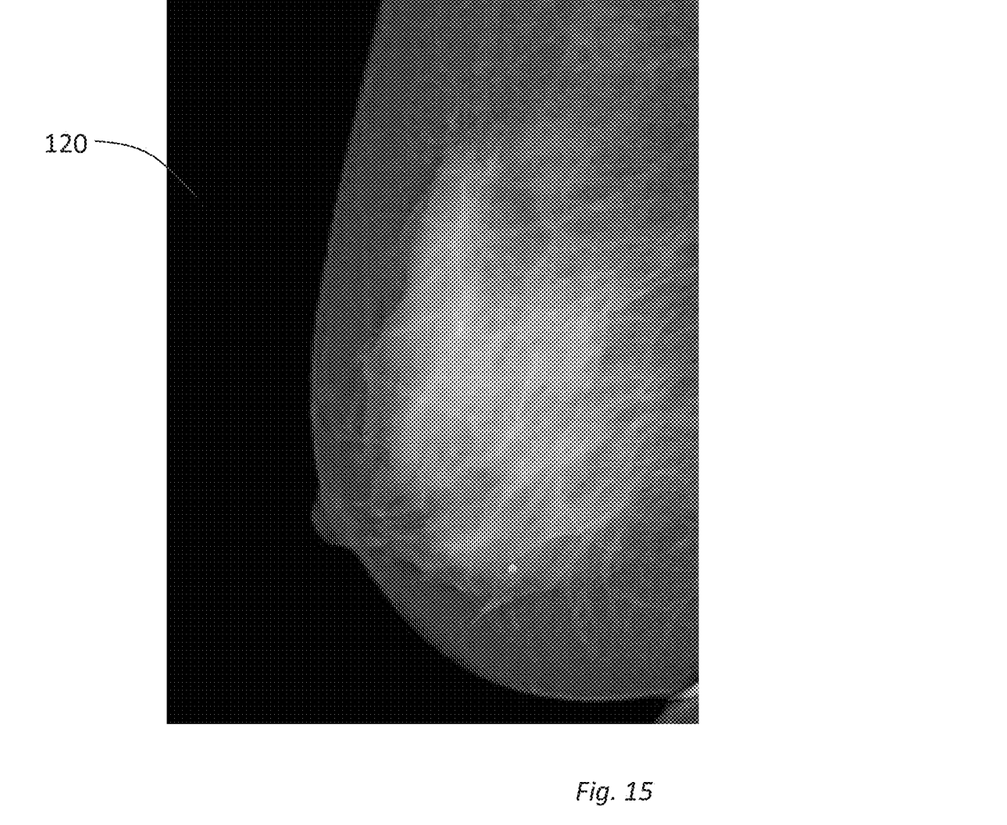
FIG. 15 is an x-ray image created from the weight blended breast image of FIG. 14 after image enhancement.

Experimental results illustrated in FIGS. 11-15 show that the weight exponent values, in Equation (4), of we=0.2 and wc=0 produces good results. In particular, FIG. 11 shows a lower-exposure breast image 112 and the same breast in a higher exposure image 114. FIG. 12 shows the images of FIG. 11 in a magnified view. FIG. 13 is an average of the lower exposure 112 and higher exposure 114 (producing image 116) and a weight blending of the lower exposure 112 and higher exposure 114 prepare according to the methods described above (producing image 118). FIG. 14 shows the images of FIG. 13 in a magnified view. FIG. 15 is an image 120 created from the weight blended breast image 118 after image enhancement.

Figure 16:
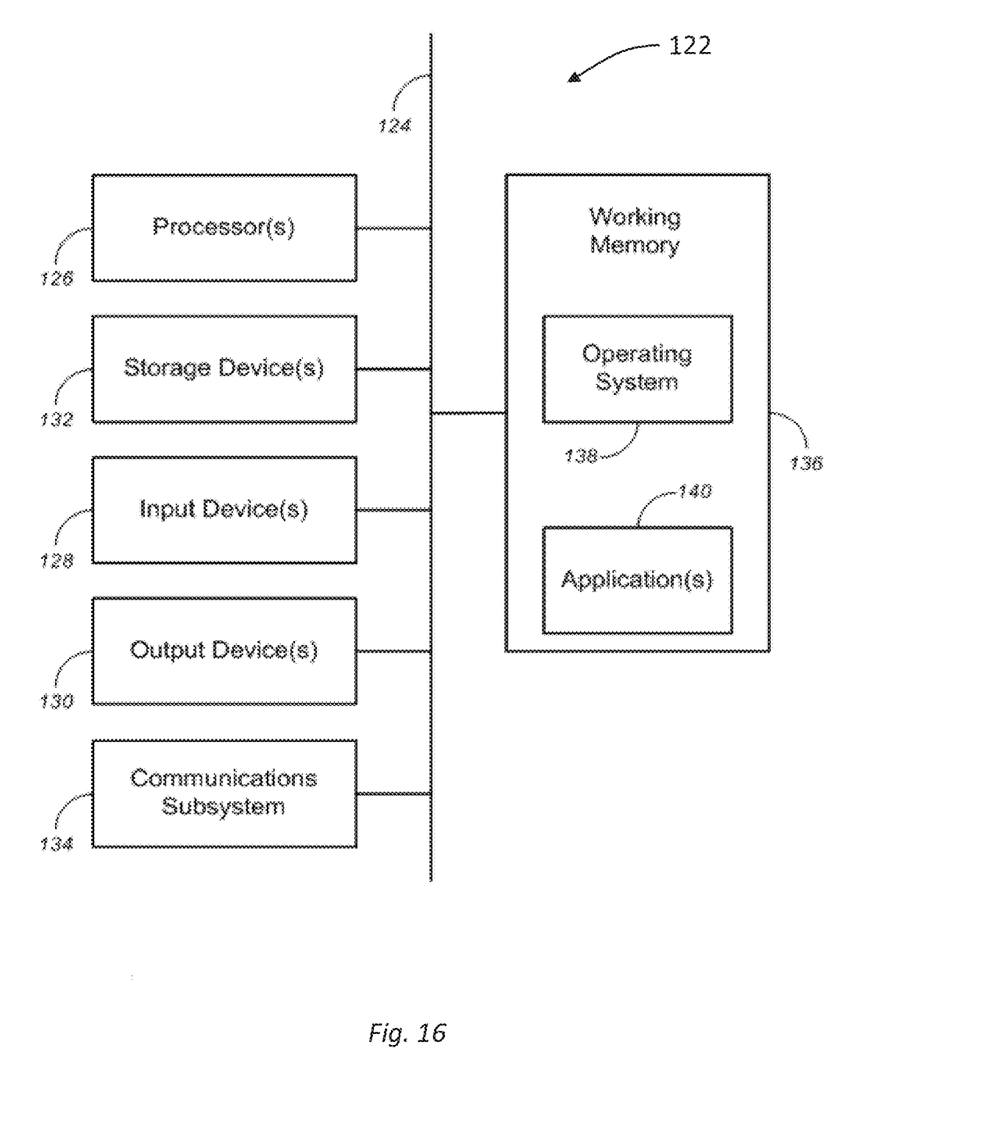
FIG. 16 is a functional block diagram representation of a data/image processing system associated with a mammography system.

Some embodiments disclosed herein include a system or apparatus having a data processing or image processing device or element. One representative data processing or image processing device is illustrated in FIG. 16. The data/image processing system 122 is shown comprising hardware elements that can be electrically coupled via a bus 124 (or may otherwise be in communication, as appropriate). The hardware elements may include one or more processors 126, including without limitation one or more general-purpose processors and/or one or more special-purpose processors (such as digital signal processing chips, graphics acceleration processors, and/or the like); one or more supplemental input devices 128, which can include without limitation a mouse, a keyboard and/or the like; and one or more output devices 130, which can include without limitation a display device, a printer and/or the like.

The data/image processing system 122 may further include (and/or be in communication with) one or more storage devices 132, which can comprise, without limitation, local and/or network accessible storage, and/or can include, without limitation, a disk drive, a drive array, an optical storage device, solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The data/image processing system 122 might also include a communications subsystem 134, which can include without limitation a modem, a network card (wireless or wired), an infra-red communication device, a wireless communication device and/or chipset (such as a Bluetooth™ device, an 802.11 device, a WiFi device, a WiMax device, a WWAN device, cellular communication facilities, etc.), and/or the like. The communications subsystem 134 may permit data to be exchanged with a network (such as the network described below, to name one example), with other computer systems, and/or with any other devices described herein. In many embodiments, the data/image processing system 122 will further comprise a working memory 136, which can include a RAM or ROM device, as described above.

The data/image processing system 122 also may comprise software elements, shown as being currently located within the working memory 136, including an operating system 138, device drivers, executable libraries, and/or other code, such as one or more application programs 140, which may comprise computer programs provided by various embodiments, and/or may be designed to implement methods, and/or configure systems, provided by other embodiments, as described herein. Merely by way of example, one or more procedures described with respect to the method(s) discussed below might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be encoded and/or stored on a non-transitory computer readable storage medium, such as the storage device(s) 132 described above. In some cases, the storage medium might be incorporated within a computer system, such as the data/image processing system 122. In other embodiments, the storage medium might be separate from a computer system (i.e., a removable medium, such as a compact disc, etc.), and/or provided in an installation package, such that the storage medium can be used to program, configure and/or adapt a general purpose computer with the instructions/code stored thereon. These instructions might take the form of executable code, which is executable by the data/image processing system 122 and/or might take the form of source and/or installable code, which, upon compilation and/or installation on the data/image processing system 122 (e.g., using any of a variety of generally available compilers, installation programs, compression/decompression utilities, etc.) then takes the form of executable code.

The terms "machine readable medium" and "computer readable medium," as used herein, refer to any medium that participates in providing data that causes a machine to operation in a specific fashion. In an embodiment implemented using the data/image processing system 122, various computer readable media might be involved in providing instructions/code to processor(s) 126 for execution and/or might be used to store and/or carry such instructions/code (e.g., as signals). In many implementations, a computer readable medium is a non-transitory, physical and/or tangible storage medium. Such a medium may take many forms, including but not limited to, non-volatile media, volatile media, and transmission media. Non-volatile media includes, for example, optical and/or magnetic disks, such as the storage device(s) 132. Volatile media includes, without limitation, dynamic memory, such as the working memory 136. Transmission media includes, without limitation, coaxial cables, copper wire and fiber optics, including the wires that comprise the bus 124, as well as the various components of the communication subsystem 134 (and/or the media by which the communications subsystem 134 provides communication with other devices). Hence, transmission media can also take the form of waves (including without limitation radio, acoustic and/or light waves, such as those generated during radio-wave and infra-red data communications).

Common forms of physical and/or tangible computer readable media include, for example, a floppy disk, a flexible disk, a hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read instructions and/or code.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the disclosed embodiments have been particularly shown and described with reference to a number of alternatives, it would be understood by those skilled in the art that changes in the form and details may be made to the various embodiments disclosed herein without departing from the spirit and scope of the disclosed embodiments and that the various embodiments disclosed herein are not intended to act as limitations on the scope of the claims. All references cited herein are incorporated in their entirety by reference.

The description of the present disclosed embodiments has been presented for purposes of illustration and description, but is not intended to be exhaustive or limiting of the disclosed embodiments to the form disclosed. The scope of the present disclosed embodiments is limited only by the scope of the following claims. Many modifications and variations will be apparent to those of ordinary skill in the art. The embodiment described and shown in the figures was chosen and described in order to best explain the principles of the disclosed embodiments, the practical application, and to enable others of ordinary skill in the art to understand the disclosed embodiments for various embodiments with various modifications as are suited to the particular use contemplated.

What is claimed is:

1. A method of imaging a breast comprising:
   providing an x-ray source;
   providing a full field digital x-ray detector;
   acquiring a sequence of sub-images having differing exposure parameters by projecting x-rays from the source to the detector while varying an x-ray beam energy between a first sub-image and a second sub-image of the sequence of sub images;
   limiting a frame integration time of the first sub-image to a frame integration time which is less than a frame integration time determined to cause sensor saturation when the sensor is unobstructed; and
   combining all of the sub-images of the sequence of sub-images into a two-dimensional composite mammography image having greater dynamic range than the dynamic range of any single sub-image.

2. The method of claim 1 further comprising providing a constant frame integration time between the first sub-image of the sequence of sub-images and the second sub-image of the sequence of sub-images.

3. The method of claim 1 further comprising varying a frame integration time between the first sub-image of the sequence of sub-images and the second sub-image of the sequence of sub-images.

4. The method of claim 1 further comprising causing the frame integration time of the second sub-image to be:
   greater than the frame integration time of the first sub-image; and
   equal to or less than the frame integration time of the first sub-image multiplied by a projected signal level at a selected location for the composite mammography image showing a selected dense tissue divided by the measured signal level at the selected location of the first sub-image showing the selected dense tissue.

5. The method of claim 1 further comprising determining an exposure parameter of one or more sub-images prior to acquiring the sequence of sub-images.

6. The method of claim 5 wherein determining an exposure parameter of one or more sub-images comprises determining a sub-exposure integration time or a sub-exposure irradiation level.

7. An apparatus for imaging a breast comprising:
   an x-ray source;
   an x-ray detector; and
   image processing apparatus configured to:
   acquire a sequence of sub-images having differing exposure parameters by projecting x-rays from the x-ray source to the detector while varying an x-ray beam energy between a first sub-image and a second sub-image of the sequence of sub images;
   limit a frame integration time of the first sub-image to a frame integration time which is less than a frame integration time determined to cause sensor saturation when the sensor is unobstructed; and
   combine all of the sub-images of the sequence of sub-images into a two-dimensional composite mammography image having greater dynamic range than the dynamic range of any single sub-image.

8. The apparatus of claim 7 wherein the image processing apparatus is further configured to provide a constant frame integration time between the first sub-image of the sequence of sub-images and the second sub-image of the sequence of sub-images.

9. The apparatus of claim 7 wherein the image processing apparatus is further configured to vary a frame integration time between the first sub-image of the sequence of sub-images and the second sub-image of the sequence of sub-images.

10. The apparatus for imaging a breast of claim 7 wherein the image processing apparatus is further configured to cause the frame integration time of the second sub-image to be:
    greater than the frame integration time of the first sub-image; and
    equal to or less than the frame integration time of the first sub-image multiplied by a projected signal level at a selected location for the composite mammography image showing a selected dense tissue divided by the measured signal level at the selected location of the first sub-image showing the selected dense tissue.

11. The apparatus for imaging a breast of claim 7 wherein the image processing apparatus is further configured to combine the sub-images into a two-dimensional composite mammography image by adding the sub-images.

12. A method of imaging a breast comprising:
providing an x-ray source;
providing a full field digital x-ray detector having pixels with an electron well density below around 500 electrons per square micron;
acquiring a sequence of sub-images having differing exposure parameters by projecting x-rays from the source to the detector; and
combining all of the sub-images of the sequence of sub-images into a two-dimensional composite mammography image having greater dynamic range than the dynamic range of any single sub-image.

13. The method of claim 12 wherein the sequence of sub-images having differing exposure parameters is acquired while varying an x-ray beam energy between a first sub-image and a second sub-image of the sequence of sub images.

14. The method of claim 13 further comprising providing a constant frame integration time between the first sub-image of the sequence of sub-images and the second sub-image of the sequence of sub-images.

15. The method of claim 12 further comprising varying a frame integration time between the first sub-image of the sequence of sub-images and the second sub-image of the sequence of sub-images.

16. The method of claim 15 limiting the frame integration time of the first sub-image to a frame integration time which is less than a frame integration time determined to cause sensor saturation when the sensor is unobstructed.

17. The method of claim 16 further comprising causing the frame integration time of the second sub-image to be:
greater than the frame integration time of the first sub-image; and
equal to or less than the frame integration time of the first sub-image multiplied by a projected signal level at a selected location for the composite mammography image showing a selected dense tissue divided by the measured signal level at the selected location of the first sub-image showing the selected dense tissue.

18. The method of claim 12 wherein the sequence of sub-images having differing exposure parameters is acquired while varying an exposure level between a first sub-image and a second sub-image of the sequence of sub-images, wherein the exposure level includes an exposure duration, an x-ray beam energy, an x-ray tube current, or combinations thereof.

19. The method of claim 12 further comprising determining an exposure parameter of one or more sub-images prior to acquiring the sequence of sub-images.

20. The method of claim 19 wherein determining an exposure parameter of one or more sub-images comprises determining a sub-exposure integration time or a sub-exposure irradiation level.

21. The method of claim 20 wherein the determination of an exposure parameter is based upon one or more of x-ray beam quality, x-ray beam intensity, information about the imaged object, breast thickness, patient age and the response of the detector.

22. An apparatus for imaging a breast comprising:
an x-ray source;
an x-ray detector including pixels having an electron well density below around 500 electrons per square micron; and
an image processing apparatus configured to:
acquire a sequence of sub-images having differing exposure parameters by projecting x-rays from the x-ray source to the detector;
combine all of the sub-images of the sequence of sub-images into a two-dimensional composite mammography image having greater dynamic range than the dynamic range of any single sub-image.

23. The apparatus of claim 22 wherein the image processing apparatus is further configured such that the sequence of sub-images having differing exposure parameters is acquired while varying an x-ray beam energy between a first sub-image and a second sub-image of the sequence of sub images.

24. The apparatus of claim 23 wherein the image processing apparatus is further configured to provide a constant frame integration time between the first sub-image of the sequence of sub-images and the second sub-image of the sequence of sub-images.

25. The apparatus of claim 22 wherein the image processing apparatus is further configured to vary a frame integration time between the first sub-image of the sequence of sub-images and the second sub-image of the sequence of sub-images.

26. The apparatus of claim 25 wherein the image processing apparatus is further configured to limit the frame integration time of the first sub-image to a frame integration time which is less than a frame integration time determined to cause sensor saturation when the sensor is unobstructed.

27. The apparatus of claim 26 wherein the image processing apparatus is further configured to provide cause the frame integration time of the second sub-image to be:
greater than the frame integration time of the first sub-image; and
equal to or less than the frame integration time of the first sub-image multiplied by a projected signal level at a selected location for the composite mammography image showing a selected dense tissue divided by the measured signal level at the selected location of the first sub-image showing the selected dense tissue.

28. The apparatus of claim 22 wherein the sequence of sub-images having differing exposure parameters is acquired while varying an exposure level between a first sub-image and a second sub-image of the sequence of sub-images, wherein the exposure level includes an exposure duration, an x-ray beam energy, an x-ray tube current, or combinations thereof.

* * * * *